United States Patent [19]

Broersma, Jr. et al.

[11] 4,343,809

[45] Aug. 10, 1982

[54] METHOD OF INHIBITING SICKLING OF SICKLE ERYTHROCYTES EMPLOYING 2-((HALOPHENOXY)METHYL)-2-IMIDAZOLINES

[75] Inventors: Robert J. Broersma, Jr., Noblesville, Ind.; Gayle A. Spittka, Midland, Mich.

[73] Assignee: The Dow Chemical Company, Midland, Mich.

[21] Appl. No.: 200,247

[22] Filed: Oct. 24, 1980

[51] Int. Cl.$^3$ ............................................. A61K 31/415
[52] U.S. Cl. ................................................. 424/273 R
[58] Field of Search ..................................... 424/273 R

[56] References Cited
PUBLICATIONS

Raper, *Ann. Soc. Belge Med. Trop.*, 1969, 49, 2, 205–210.

*Primary Examiner*—Frederick E. Waddell

[57] ABSTRACT

Method for inhibiting the sickling of sickle erythrocytes in blood by contacting the sickle erythrocytes with a compound of the formula:

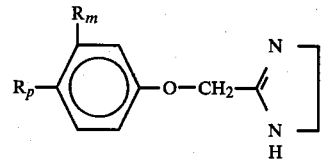

or a pharmaceutically-acceptable salt thereof, wherein $R_m$ represents hydrogen or alkyl; and $R_p$ represents chloro, bromo, fluoro or iodo.

3 Claims, No Drawings

METHOD OF INHIBITING SICKLING OF SICKLE ERYTHROCYTES EMPLOYING 2-((HALOPHENOXY)METHYL)-2-IMIDAZOLINES

BACKGROUND OF THE INVENTION

In the adult human most hemoglobin is hemoglobin A (Hb-A) consisting of two alpha and two beta polypeptide chains. Certain individuals have an abnormal hemoglobin known as hemoglobin S (Hb-S) which results from the hereditary substitution of valine for glutamic acid in the sixth amino acid position in the beta polypeptide chains of hemoglobin. The proportion of Hb-S to Hb-A in such an individual depends upon whether the individual is a homozygous or heterozygous individual. The tendency toward sickling, that is, the formation of abnormally shaped erythrocytes in which the erythrocytes assume a sickle shape, depends upon the amount of Hb-S in the erythrocyte and the level of oxygen tension. Erythrocytes with 100 percent Hb-S sickle at physiological oxygen tensions, however as the amount of Hb-A increases and Hb-S decreases progressively lower oxygen tensions are required to induce sickling. The homozygous individual has 80 to 100 percent of the hemoglobin in the Hb-S form and sickling occurs at ordinary oxygen tensions. Such individuals are said to have sickle cell disease. Heterozygous individuals are said to possess sickle cell trait since only 25 to 40 percent of their hemoglobin is Hb-S, and sickling occurs only at unusually low oxygen tensions.

The presence of sickled erythrocytes can have severe implications since sickled erythrocytes encounter mechanical difficulties in moving through small vessels and the consequent stasis and jamming of these cells can lead to thrombosis and tissue anoxia. In addition, because of the sickled erythrocytes' increased mechanical fragility, hemolysis results. S. L. Robbins and M. Angell, "Basic Pathology", W. B. Saunders Company, Philadelphia, London, Toronto, 1971, pp. 127 and 282.

A treatment or test in which the sickling of red blood cells prone to sickle (sickle erythrocytes) is inhibited or reversed would be useful in the treatment of afflicted individuals or for the study of the sickling phenomenon.

SUMMARY OF THE INVENTION

It has now been discovered that the sickling in blood of red blood cells prone to sickle can be inhibited by contacting the sickle erythrocytes in blood with an effective amount of a compound of the formula:

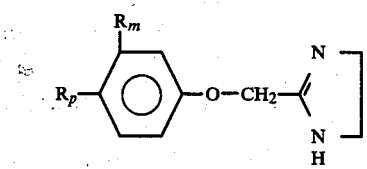

or a pharmaceutically-acceptable salt thereof, wherein $R_m$ represents hydrogen or alkyl; and $R_p$ represents chloro, bromo, fluoro or iodo.

As used herein, the term "alkyl" refers to an alkyl group of from 1 to 3 carbon atoms such as methyl, ethyl, propyl and isopropyl.

"Pharmaceutically-acceptable salt" refers to nontoxic acid addition salts of the compounds, the anions of which are relatively innocuous to mammals at exposure levels or dosages consistent with activity or use of the compounds, so that the beneficial effects of the free base are not vitiated by the side effects, or mammalian toxicity, ascribable to the anions. Pharmaceutically-acceptable salts include those derived from mineral acids such as hydrochloric and sulfuric acids and from organic acids such as lactic, maleic, succinic, fumaric, glutaric, citric, malic, p-toluenesulfonic, methanesulfonic and tartaric acids.

As used herein, an effective amount of the compound represented by formula I or a pharmaceutically-acceptable salt thereof is that amount of the compound or its pharmaceutically-acceptable salt which when employed according to the method of the present invention is sufficient to inhibit the sickling of sickle erythrocytes in blood. As used in the specification and claims, "inhibiting" means inhibiting the formation of sickle morphology and also includes actively reversing sickled cells to a more normal or typical morphology, in cases in which sickling has already occurred. The compounds used in the practice of the present invention are therefore particularly useful in the study of the sickling phenomenon, in the investigation of the effects of chemical substances on erythrocytes and has potential usefulness as a treatment for individuals subject to the sickling phenomenon.

DETAILED DESCRIPTION OF THE INVENTION

The compounds used in the practice of the present invention, i.e., the compounds of formula I or a pharmaceutically-acceptable salt thereof, are prepared by reacting the appropriate substituted-phenoxyacetonitrile represented by the formula:

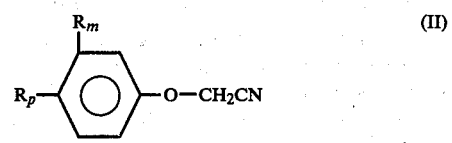

wherein $R_m$ and $R_p$ are defined as for formula I, with ethylenediamine p-toluenesulfonate. The reaction is conveniently accomplished employing a procedure similar to that used for the preparation of 2-((halophenoxy)-methyl)-2-imidazolines, as described in U.S. Pat. No. 3,449,356. In preparing the 2-imidazoline compounds of formula I, the appropriate acetonitrile, i.e., formula II compound, and the ethylenediamine p-toluenesulfonate are mixed and heated together in an inert organic solvent, such as 1,2-dichlorobenzene for a time sufficient to obtain the desired 2-imidazoline p-toluenesulfonate salt. The reaction is preferably carried out under an inert atmosphere, accomplished by passing nitrogen through the reaction mixture to carry off the ammonia formed during the reaction.

The 2-imidazoline p-toluenesulfonate salt can be separated from the reaction mixture using known procedures such as adjustment of reaction mixture concentration, filtration, centrifugation and decantation. The 2-imidazoline p-toluenesulfonate salt can be purified by conventional procedures such as recrystallization and washing.

Alternatively, the 2-imidazoline p-toluenesulfonate salt can be converted to the free base from (i.e., free imidazoline) by hydrolysis in aqueous base. The free base is then separated by extraction with an organic solvent such as methylene chloride ($CH_2Cl_2$) or chloro-form (CHCl₃), followed by evaporation of the solvent. Purification of the free base is accomplished by conventional methods such as recrystallization or the free base can be converted to a pharmaceutically-acceptable salt by treating the free base with the appropriate organic or mineral acid. The pharmaceutically-acceptable salt can be purified by known procedures such as recrystallization.

The substituted-phenoxyacetonitrile reactant, illustrated by formula II, is prepared by reacting a substituted-phenol of the formula:

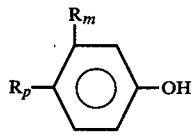

(III)

wherein $R_m$ and $R_p$ are as defined for formula I, and chloroacetonitrile in the presence of a base, such as potassium carbonate ($K_2CO_3$).

The reaction is accomplished by heating the reactants, usually at about 70°–90° C., in an inert organic solvent such as dimethyl sulfoxide for a time sufficient to obtain the desired acetonitrile starting material. The acetonitrile is recovered and purified by conventional procedures such as those described herein.

The following examples are included to further illustrate the invention but are not to be construed as a limitation thereon.

EXAMPLE 1

2-(((4-Chloro-m-tolyl)oxy)methyl)-2-imidazoline (a) Preparation of 4-chloro-m-tolyloxyacetonitrile A mixture of 71.25 grams (g) of 2-chloro-5-hydroxytoluene, 98.0 g of anhydrous potassium carbonate, 40 g of chloroacetonitrile and 100 milliliters (ml) of dimethyl sulfoxide was placed in a 500 ml round-bottom three-necked flask and stirred. An ice bath was used to maintain the temperature at 70°–80° C. for approximately 20 minutes and then a heating mantle was used to keep the reaction mixture temperature at 70°–80° C. for an additional 2 hours. The reaction mixture was then poured into 2500 ml of ice water which resulted in solids precipitating. The mixture was filtered and the solids washed with water. The solids were recrystallized by dissolving the solids in approximately 200 ml of boiling cyclohexane, treating the resulting solution with activated charcoal and then filtering. The filtrate was cooled and then filtered to obtain 78.3 g of 4-chloro-m-tolyloxyacetonitrile, having a melting point (m.p.) of 44°–45° C.

(b) Preparation of 2-(((4-chloro-m-tolyl)oxy)methyl)-2-imidazoline

A mixture of 36.3 g of 4-chloro-m-tolyloxyacetonitrile, 46.6 g of ethylenediamine p-toluenesulfonate and 150 ml of 1,2-dichlorobenzene was heated with stirring in a 500 ml round-bottomed three-necked flask at reflux under a small flow of nitrogen for 1.5 hours, essentially as described in U.S. Pat. No. 3,449,356. The reaction mixture was cooled, diluted with methylene chloride and the solids filtered off. The solids were slurried in water and then basified with 5 normal (N) sodium hydroxide and then filtered. The solids were washed well with water and dried to obtain 42.0 g of the crude product, m.p. 91°–95° C. A 19.5 g portion of the crude product was put in solution in approximately 150 ml of boiling toluene, treated with activated charcoal and filtered. The filtrate was cooled and then filtered, which gave 14.7 g of purified 2-(((4-chloro-m-tolyl)oxy)methyl)-2-imidazoline, m.p. 90°–92° C.

EXAMPLE 2

2-((4-Chlorophenoxy)methyl)-2-imidazoline Hydrochloride (a) Preparation of 4-chlorophenoxyacetonitrile A mixture of 64.25 g of 4-chlorophenol, 98 g of anhydrous potassium carbonate, 40 g of chloroacetonitrile and 100 ml of dimethyl sulfoxide was heated with stirring in a 500 ml round-bottomed three-necked flask at 70°–80° C. for 3.0 hours. The reaction mixture was then poured into ice and water. After the ice melted, the mixture was filtered and the product washed well with water which gave 77.5 g of 4-chlorophenoxyacetonitrile.

(b) Preparation of 2-((4-chlorophenoxy)methyl)-2-imidazoline hydrochloride

A mixture of 25.1 g of 4-chlorophenoxyacetonitrile, 35.0 g of ethylenediamine p-toluenesulfonate and 112.5 ml of 1,2-dichlorobenzene was heated with stirring in a 500 ml round-bottomed three-necked flask at reflux (178° C.) for 1.0 hour. The reaction mixture was cooled, then diluted with methylene chloride and filtered. The crystals that were obtained were dried in a vacuum oven. The dried crystals were slurried in water, the resulting slurry basified and then extracted with methylene chloride. The methylene chloride extract was treated with diatomaceous earth and activated charcoal and then filtered. The methylene chloride was evaporated and 27.4 g of the free imidazoline obtained, m.p. 116°–118° C. The free imidazoline was then put in solution in isopropyl alcohol and acidified with HCl in isopropyl alcohol. The mixture was then cooled and filtered which gave 27.4 g of 2-((4-chlorophenoxy)methyl)-2-imidazoline hydrochloride, m.p. 185°–186° C.

In practicing the method of the invention, the imidazoline compounds are brought into contact with sickle erythrocytes, typically by introducing an effective amount of the compound into the blood of a mammal having blood containing erythrocytes subject to sickling. Introducing an effective sickle inhibiting amount of the above-noted compound or pharmaceutically-acceptable salt into the blood of such a mammal can be carried out directly, e.g., by direct addition to blood samples, or indirectly, by administering the compound to the mammal in a manner effective to provide the sickle inhibiting concentration in the blood stream.

The compound or pharmaceutically-acceptable salt thereof would be introduced using a route of administration which provides an effective but non-toxic concentration of the compound in the blood, either by oral ingestion or direct administration as, for example, intravenous infusion or injection. The amount to be administered would vary depending on the compound or pharmaceutically-acceptable salt employed, the type of erythrocyte sickling inhibition or reversal desired, the size and nature of the mammal, and the manner of contacting the blood. When used to inhibit erythrocyte sickling in a mammal, the quantity of compound or pharmaceutically-acceptable salt to be administered in particular instances can be determined by routine procedures, such as studies of the concentration of the compound in the blood obtained at various time intervals after administration, using various methods of administration, and in vitro studies of the anti-sickling effect obtained with various concentrations of the compound in the particular blood in question.

The compounds described herein were tested in an "Oxygen-Affinity Assay" to measure the ability of the compound to influence the Hb-S oxygen affinity. There is a relationship between oxygen binding and Hb-S gelation and thus a measure of oxygen affinity is an index of Hb-S aggregation within the red blood cell. Hemoglobin S polymers decrease the overall oxygen affinity. Thus a return to normal of Hb-S oxygen affinity is a measure of decreased gelation.

For measurements of oxygen equilibria whole Hb-S blood was equilibrated in a tonometer at 37° C. and measurements were made in the presence of a 10 millimolar (mM) concentration of the test compound. The compound 2-(((4-chloro-m-tolyl)oxy)methyl)-2-imidazoline was also tested at a 5 mM concentration. The whole blood pH, oxygen tension, and blood $PO_2$ were measured. The percentage of oxygen saturation was plotted against the partial pressure of oxygen (mm Hg). The $P_{50}$ value (oxygen tension at 50% saturation) was determined for each control and treated whole blood sample and the difference ($\Delta P_{50}$) between the conrol and treated whole blood sample noted. As used herein, a negative $\Delta P_{50}$ represents a change toward a normal Hb-S oxygen affinity and thus is a measure of the test compound's ability to inhibit the sickling of sickle erythrocytes. The results of the Oxygen-Affinity Assays are presented in Table 1.

TABLE 1
| Compound Example Number | Oxygen-Affinity Assay $\Delta P_{50}$ | |
| --- | --- | --- |
| | 10 mM | 5 mM |
| 1 | −10.7 | −18 |
| 2 | −4.5 | |

The data in Table 1 shows that the test compounds at a 10 mM concentration exhibited a negative $\Delta P_{50}$ which indicates that the test compound inhibited the sickling of sickle erythrocytes. The test compound 2-(((4-chloro-m-tolyl)oxy)methyl)-2-imidazoline also inhibited the sickling of sickle erythrocytes at a 5 mM concentration.

What is claimed is:

1. A method for inhibiting the sickling of red blood cells prone to sickle in blood containing said cells which comprises introducing into said blood an effective sickle inhibiting amount of a compound of the formula:

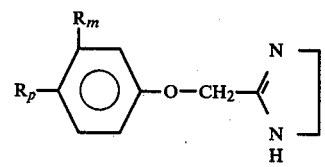

or a pharmaceutically-acceptable salt thereof, wherein $R_m$ represents hydrogen or alkyl; and $R_p$ represents chloro, bromo, fluoro or iodo.

2. The method of claim 1 wherein the compound is 2-(((4-chloro-m-tolyl)oxy)methyl)-2-imidazoline or a pharmaceutically-acceptable salt thereof.

3. The method of claim 1 wherein the compound is 2-((4-chlorophenoxy)methyl)-2-imidazoline or a pharmaceutically-acceptable salt thereof.

* * * * *